United States Patent [19]

Yamazaki

[11] Patent Number: 5,011,915

[45] Date of Patent: Apr. 30, 1991

[54] PROCESS FOR PURIFYING RECOMBINANT HEPATITIS ANTIGENS

[75] Inventor: Shigeko Yamazaki, Hatfield, Pa.

[73] Assignee: Merck & Co., Inc., Rahway, N.J.

[21] Appl. No.: 113,582

[22] Filed: Oct. 26, 1987

[51] Int. Cl.$^5$ ............................................. C07K 3/26
[52] U.S. Cl. ..................................... 530/414; 530/412; 530/418; 530/419; 530/422; 530/300; 530/350; 530/824; 530/371; 424/89
[58] Field of Search ............ 530/412, 414, 417, 418, 530/419, 422, 300, 350, 371, 824; 424/89

[56] References Cited

U.S. PATENT DOCUMENTS

| | | | |
|---|---|---|---|
| 4,578,269 | 7/1986 | Morein | 424/89 |
| 4,624,918 | 11/1986 | Hershberg | 424/89 |
| 4,666,713 | 5/1987 | Stelly et al. | 429/89 |
| 4,683,293 | 7/1987 | Craig | 514/2 |
| 4,683,294 | 7/1987 | Wijnendaele et al. | 530/419 |
| 4,738,926 | 4/1988 | Hamada et al. | 436/543 |
| 4,855,055 | 8/1989 | Lin et al. | 424/89 |
| 4,894,444 | 1/1990 | Scattergood et al. | 530/412 |
| 4,902,783 | 2/1990 | Goda et al. | 530/412 |

FOREIGN PATENT DOCUMENTS

| | | |
|---|---|---|
| 0072318 | 2/1983 | European Pat. Off. . |
| 0114506 | 1/1984 | European Pat. Off. . |
| 0105149 | 4/1984 | European Pat. Off. . |
| 0171908 | 2/1986 | European Pat. Off. . |
| 0198474 | 10/1986 | European Pat. Off. . |
| 0226846 | 7/1987 | European Pat. Off. . |
| WO87/01128 | 2/1987 | PCT Int'l Appl. . |

OTHER PUBLICATIONS

Wamper et al., *PNAS* 82, 1985, pp. 6830–6834.
Neurath et al., *Nature* 315, 1985, pp. 154–156.
Salstrom et al., CA vol. 106, 1987, #28525f.
Damoddran et al., *BBA* (801), 1984, pp. 416–423.
Ifolm et al., Gene 42, 1986, pp. 169–173.
Skelly et al., *Nature* 210, 1981, pp. 51–54.
Meyhack, B. Chem. Abs. 103, 136419 (1985?).
Holm, C. et al., Gene 42, 169 (1986).
Itoh, Y. et al., Biochem. Biophys. Res. Comm. 138, 268 (1986).
Neurath, A. R. et al., Nature 315, 154 (1985).
Hitzeman, R. A. et al., Nucleic Acids Res. 11, 2745 (1983).

*Primary Examiner*—Garnett D. Draper
*Attorney, Agent, or Firm*—Roy D. Meredith; Charles M. Caruso

[57] ABSTRACT

Methods of purifying recombinant surface antigen of hepatitis B virus are disclosed. In one protocol, purification is achieved by selective extraction of the antigen from yeast membranes, followed by solubilization with urea and dithiothreitol.

15 Claims, No Drawings

PROCESS FOR PURIFYING RECOMBINANT HEPATITIS ANTIGENS

RELATED APPLICATIONS

This application is related to Ser. No. 636,514, filed Aug. 1, 1984, now U.S. Pat. No. 4,707,542 Ser. No. 019,820, filed Feb. 27, 1987, now abandoned.

INTRODUCTION

Hepatitis B surface antigen often occurs as a glycoprotein protein complex that confers immunity against the pathological effects of subsequent infection by hepatitis B virus. Sources for safe, rapid and inexpensive manufacture of the antigen for vaccination purposes have been limited to serum or plasma from patients who synthesize large quantities of the requisite antigen, usually in the form of 22 nm particles. With the advent of recombinant DNA techniques, DNA coding for the surface antigen is inserted into yeast, *E. coli* and other cellular systems, then expressed. The resulting polypeptide product varies substantially with the DNA construction used as well as the host or cellular systems employed to express the inserted DNA.

The HB virion is composed of two groups of structural proteins, the core proteins and the envelope or surface ("S") proteins. In addition to being the major surface proteins of the virion, i.e., Dane particle, the "S" proteins are the sole constituents of Australia antigen, or 22 nm particles. The "S" proteins are the translational products of a large open reading frame (ORF) encoding 389–400 amino acids, depending upon serotype. This ORF is demarcated into three domains, each of which begins with an ATG codon that is capable of functioning as a translational initiation site in vivo. These domains are referred to as pre-S1 (108–119 amino acids), pre S2 (55 amino acids), and S (226 amino acids) in their respective 5'-3' order in the gene. The six protein products derived from this ORF have the following compositions:

(1) gp42 (42,000 dalton glycoprotein)=pre-S1/S2/S (meaning pre-S1 contiguous with pre-S2, contiguous with S),
(2) p39 (p=protein)=pre-S1/S2/S,
(3) gp36=pre-S2/S (two glycosylation sites),
(4) gp33=pre-S2/S (one glycosylation site),
(5) gp27=S (one glycosylation site),
(6) p24=S.

All six proteins are present to an approximately equimolar extent in the HBV Dane particle. In the 22 nm particle, the 4 smaller proteins are present to an approximately equimolar extent, while gp42 and p39 are present in at most one or a few molecules per particle. The pre-S1 and pre-S2 regions may have functions of promoting secretion of the S region. For reviews of these fundamental properties of the protein, see Tiollais, P. et al., Science 213, 406 (1981) and Milich, D. R. et al., Proc. Natl. Acad. Sci. 82, 8168 (1985).

The pre-S2 region of the hepatitis B antigen comprises about 55AA (amino acid) residues. Its presence provides a dominant epitope that is more immunogenic in vivo than epitopes of the S protein, according to Neurath, A. R. et al., Science 224, 392 (1984), Neurath, A. R. et al., Nature 315, 154 (1985), and Milich, D. R. et al., supra. The pre-S2 poly-peptide also has receptor-like properties for polymerized human serum albumin (pHSA), a trait also possessed by liver cells which are known to bind pHSA, Machida, A. et al., Gastroenterology 86, 910 (1984).

Since the presence of pre-S2 sequences in the surface antigen is a desirable property for the purposes of immunization, expression systems have been developed for the expression of pre-S1/-S2/S protein and other variants. See, for example, U.S. patent application No. 824,405, filed Jan. 31, 1986, now U.S. Pat. No. 4,816,564. The methods of the present invention relate to selective extraction of recombinant surface antigen of hepatitis B virus (rHbsAg) from yeast cell membranes, followed by solubilization. Partially purified rHbsAg precipitates are solubilized by a combined and simultaneous treatment of urea and DTT. Precipitates or other insoluble entities frequently occur in the process of purifying rHbsAg from yeast and other expression systems. The present invention provides methods of rendering soluble such precipitates for the purposes of making a better and cheaper vaccine against hepatitis-associated diseases.

The technical advantages of selectively extracting and solubilizing the partially purified recombinant surface antigen include higher yield and greater purity. The solubilized product is also more stable. The techniques of selective extraction and solubilization are rapid and simple.

Purification of recombinant proteins not infrequently requires new methods or novel combinations of old methods, since the composition of the source for recombinant forms e.g. yeast are different from conventional sources e.g. serum. One cannot predict what methods are useful for isolating proteins from recombinant cell cultures on the basis of the knowledge and know how of methods useful for isolating proteins from classical or otherwise conventional sources. Purification processes designed for preparing vaccines require unusual purity in the product, another indication of the unpredictability in the art. For a similar view, see U.S. Pat. No. 4,624,918.

BRIEF DESCRIPTION OF THE INVENTION

In this application there is disclosed methods of substantially purifying recombinant pre-S1/S2 hepatitis B antigen, or portion thereof, comprising the steps of
(a) taking an aliquot of yeast membrane associated antigen extract;
(b) removing the debris of the extract of step (a) by centrifugation;
(c) subjecting the supernatant to diafiltration in the presence of a solution effective to release undesired yeast membrane bound proteins, and thereafter removing said undesired yeast membrane bound proteins to yield washed yeast membrane as a retentate product;
(d) subjecting the retentate product of step (c) to a second solution effective to release the membrane bound surface antigen;
(e) subjecting the surface antigen released in step (d) to diafiltration in a third solution to promote passage of said surface antigen across the diafiltration membrane, yielding a filtrate;
(f) treating filtrate with a quantity of denaturing agent in the presence of a reducing agent effective to solubilize said filtrate; and
(g) removing the denaturing agent and the reducing agent, yielding a substantially purified recombinant pre-S1/S2/S hepatitis B antigen, or portion thereof.

The products of these methods have immunological potency and are useful as vaccines against hepatitis B.

DEFINITIONS AND ABBREVIATIONS

Specific activity: a weight-to-weight ratio of immunochemically reactive sAg to total protein.

| | |
|---|---|
| AA | amino acid |
| DTT | dithiothreitol |
| $ED_{50}$ | 50% effective dose |
| EDTA | ethylenediamine tetracetic acid trisodium salt |
| L | liter |
| Mr | mobility |
| MW | molecular weight |
| NMW | nominal molecular weight cutoff |
| pHSA | polymerized human serum albumin |
| PBS | phosphate buffered saline, 0.15M NaCl in 7 mM sodium phosphate buffer. pH about 7.2 |
| PMSF | phenylmethylsulfonyl fluoride |
| psi | pounds per square inch |
| rHbsAg | recombinant hepatitis B surface antigen |
| S | surface |
| SDS-PAGE | sodium dodecyl sulfate polyacrylamide gel electrophoresis |

DETAILED DESCRIPTION OF THE INVENTION

The processes of the present invention involve methods of purifying recombinant hepatitis B surface antigen (rHbsAg) from yeast extracts, by selective extraction of rHbsAg from yeast membranes, followed by solubilization by the combined treatment with denaturing agent(s) and reducing agents(s).

It will be understood that the novel purification processes of the present invention are applicable to a range of expressed rHbsAg, including recombinant S protein or recombinant pre-S1/S2/S protein. One principle example is rHbsAg produced by yeast cells. This system expresses S or pre-S1/S2/S amino acid sequences. Processes for the purification of other variant amino acid sequences of the S protein or pre-S1/S2/S protein are encompassed by the present invention. The processes of the present invention are designed to provide rapid and efficient methods of purifying S protein variants as well as pre-S1/S2/S protein variants, in accordance with the principles of the present invention. For example, conservative substitutions [defined as sets in Table 1 of Taylor, W. R., J. Mol. Biol. 188, 233 (1986)] in the amino acid sequence generally will not result in any substantial or novel modification of the principles and practice of the present invention. Conservative substitutions of hepatitis surface antigen are known; see Elfassi, E. et al., J. Theor. Biol. 121, 371 (1986). Alternatively, deletions within the S, pre-S1 or pre-S2 regions will not in general require any modifications of the processes for purification discussed herein. It will be understood that rHbsAg, the pre-S1/S2/S protein, surface antigen or portion thereof in this application includes any such variations in the amino acid sequence, whether by conservative substitution, deletion, or other process, provided that rHbsAg, the pre-S1/S2/S protein, the surface antigen, or portion thereof, is immunochemically reactive with antibodies specific the S protein, the 22 nm particle, Australia antigen, Dane particles or other natural form of the hepatitis surface antigen sequence.

Many yeast expression systems are clearly adequate for providing sources of the rHbsAg. The *S. cerevisiae* expression system employed herein is intended as a merely incidental source. Other yeast vectors include but are not limited to shuttle vectors, cosmid plasmids, chimeric plasmids, and those having sequences derived from 2-micron circle plasmids. A variety of promoters and other yeast transcriptional control sequences may be used to express the inserted DNA sequence coding for surface antigen, including those of GAL10 and the alpha mating factor.

The genus Saccharomyces is composed of a variety of species. Most commonly used is *Saccharomyces cerevisiae*, or baker's yeast, as a host for the recombinant DNA-mediated expression of a variety of foreign polypeptides. However, the distinctions among other species of the genus Saccharomyces are not always well defined. Many of these species are capable of interbreeding with *S. cerevisiae* and are likely to possess regulatable promoters which are analogous or identical to promoters is *S. cerevisiae*, including but not limited to GAL10, ADH2, GAP and/or alpha mating factor promoters. Therefore, it will be apparent to those skilled in the art that, for the expression of pre-S-containing polypeptides, the selection of a host strain extends to other species of the genus Saccharomyces, including but not limited to *carlsberqensis, uvarum, rouxii, montanus, kluyveri, elongisporus, norbensis, oviformis*, and *diastaticus*.

Several yeast genera, such as Hansenula, Candida, Torulopsis, and Pichia, have been shown to contain similar metabolic pathways for the utilization of methanol as a sole carbon source for growth. The gene for alcohol oxidase, an enzyme which participates in this metabolic pathway, has been isolated from *Pichia pastoris*. The *P. pastoris* alcohol oxidase promoter has been isolated and shown to be susceptible to methanol induction of expression. Such an inducible promoter is useful for the expression of polypeptides which are negatively selected in yeast. In particular, this promoter has been shown to be active on a plasmid for the inducible expression of the S domain in *P. pastoris* in particulate form. This observation highlights the ability of other yeast genera to function as hosts for the recombinant DNA-mediated expression of S polypeptides in immunologically active form. Therefore, it will be apparent to those skilled in the art that, for the expression of rHbsAg, the selection of a host strain extends to species from other genera of yeast from the Families Saccharomycetaceae and Cryptococcaceae, including, but not limited to Pichia, Candida, Hansenula, Torulopsis, Kluyveromyces, and Saccharomycopsis.

In the process of purifying hepatitis surface antigen, excessive instability and breakdown of the surface antigen has been observed. To combat this, solvents are typically buffered and also contain protease inhibitors such as PMSF and EDTA. To further reduce proteolysis, it is preferred to carry out all purification steps at about 4° C.

Typical protease inhibitors suitable for the procedures and protocols of this invention include but are not limited to metal cheating agents, heavy metal ions, SH blocking reagents, substrate like compounds of proteases or polypeptides that inhibit proteases. Some useful protease inhibitors are provided as follows:

$Ag^{++}$, $Cu^{++}$ and other heavy metal ions
antithrombin III
antithrombin III—heparin
$\alpha_1$-antitrypsin
aprotinin basic amino acids
benzamidine
bestatin
α,α'-bipyridyl, Na-fluoride
4-bromo-phenacyl bromide
chicken egg white trypsin inhibitor
chymostatin
citrate
cysteine
4-dinitrophenol diethylphosphate
DFP (diisopropylphosphofluoridate)
DTT
E-64 (Boehringer Mannheim)
EDTA and other chelating agents
formaldehyde
quanidinium chloride
heparin
hirudin
4-hydroxymercuribenzoate
iodoacetamide
iodoacetic acid
leupeptin
$\alpha_2$-macroglobulin
mercaptoethanol
p-mercuribenzoate
mercuric chloride
α-microglobulin
α-N-(p-nitrobenzyl-oxycarbonyl)-L-arginyl-chloromethyl ketone
oxalate
pepstatin from a variety of sources, including Streptomyces
1,10-phenanthroline
2-phenanthroline
phenothiazine-N-carbonyl chloride
phosphoramidone
PMSF
pyrophosphate
SH-blocking reagents
silver nitrate
soybean trypsin inhibitor
p-toluene sulfonyl fluoride
TPCK[L-1-chloro-3-(4-tosylamido)-7-amino-2-heptanonehydrochloride]
TRITON X-100 and other detergents at low concentrations
TPCK[L-1-chloro-3-(4-tosylamido)-4-phenyl-2-butanone]
trypsin inhibitor from hen egg
ZPCK (benzyloxycarbonyl-L-phenylalanine)

Buffered solutions containing one or more of the listed inhibitors may be adapted to one or more steps in the process of purifying surface antigen.

PURIFICATION

Yeast cells transformed with expression vectors coding for pre-S1/S2/S protein, S protein, or variants thereof, are grown and harvested. If storage of the cells is desired, the cells are then washed in buffer, e.g. PBS, to form a cell paste. Storage of the cell paste is typically done by freezing in liquid $N_2$.

Purification typically begins as follows. A batch of frozen cell paste is thawed and suspended in buffer containing proteolytic inhibitors, e.g. PBS in 2mM PMSF, or hypertonic phosphate buffers. Cells are then disrupted, preferably by mechanical means. The gentle bead breakage method for disruption has been found unsuitable for scale up. Disruption by a cell disrupter is the most preferred because of its rapid operation.

Yeast cell disruption results in a crude extract. It is necessary at this point to remove cell debris in the extract so that mechanical clogging in subsequent purification steps is avoided. Centrifugation at about 4,400×g for 5 minutes has been found adequate, but it is readily understood that different centrifugation speeds for different times are also possible and easily rendered operable. The presence of pre-S polypeptide epitopes can be ascertained by the binding of these epitopes to polymerized human serum albumin (pHSA) in a sandwich RIA assay with labelled antibody specific to HBV surface antigen.

Further steps in the purification process are performed on the 4,400×g supernatant remaining after the cell debris is removed from the crude extract by centrifugation at 4,400×g for 5 minutes, as described above.

SELECTIVE EXTRACTION

The process of selectively extracting rHbsAg as a membrane-bound (MB) protein from yeast cell membranes generally involves the initial removal of undesired MB proteins followed by removal and isolation of MB rHbsAg. More particularly, the steps in selective extraction of MB rHbsAg typically include:

1. subjecting the supernatant, such as the 4,400×g supernatant, to diafiltration in the presence of a solution effective to release undesired yeast membrane-bound proteins, and thereafter removing said undesired yeast membrane-bound proteins to yield washed yeast membrane as a retentate product;

2. subjecting the retentate product of step (1) to a second solution effective to release the membrane-bound surface antigen; and, 3. subjecting the surface antigen released in step (2) to diafiltration in a third solution to promote passage of said surface antigen across the diafiltration membrane; yielding a filtrate.

Prior to step (1), the soluble fraction in the supernatant is conveniently removed by ultracentrifugation, filtration, diafiltration, with or without pressure, as the case may be, to yield membrane bound material. Buffers should contain inhibitors of proteases. The preferred method of removing the soluble fraction is to pump the 4,400×g supernatant through a diafiltration unit of 0.2 μm pore size under positive pressure of about 10-15 psi, with a wash of PBS containing protease inhibitors. The pressure promotes passage of soluble material through the membrane barrier of the diafiltration unit. The practical advantage of diafiltration is that dialysis and filtration are performed together. Many types of diafiltration units are feasible for use. Release of soluble material can be monitored by optical density.

To prepare the washed yeast membranes of step (1), the membrane bound material is treated with mild denaturing agents at concentrations sufficient to release most of the MB protein without release of the MB surface antigen. Suitable agents include detergents or protein denaturants, or mixtures thereof. A variety of neutral or nonionic detergents can be used, including but not limited to detergents of the nonoxynol series, octoxynol series, polyoxyethylene alcohol series, polyoxyethylene (20) sorbitan mono-oleate series, deoxycholate, or octylglucopyranoside, and the like. Zitterionic detergents are also useful and suitable agents.

Protein denaturants that are suitable for releasing unwanted or undesired MB proteins in step (1), supra, include the generic class of compounds of the formula:

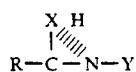

wherein
R is amino, loweralkylthio, loweralkyloxy, or sulfur;
X is amino, sulfur or oxygen; and
Y is hydrogen or amino.

This formula includes the preferred protein denaturant, guanidine.HCl, most preferably used in a concentration gradient from between about 7M to about 1M. Additional suitable protein denaturants include anions such as $ClO_4^-$ and chaotropic agents.

The preferred protocol in step (1) for preparing washed yeast membrane is to conduct diafiltration of the membrane bound material in a solution of PBS, containing protease inhibitors, with a denaturing gradient from between about 7M guanidine.HCl and about 1M guanidine.HCl.

Washed yeast membranes are then extracted in step (2) with a detergent or a protein denaturant, or mixtures thereof, with the purpose of releasing MB surface antigen. Any one of a variety of nonionic or neutral detergents are suitable for the extraction, including but not limited to detergents of the nonoxynol series, octoxynol series, polyoxyethylene alcohol series, polyoxyethylene (20) sorbitan mono-oleate series, deoxycholate, or octylglucopy ranoside, and the like. Zitterionic detergents are also useful and suitable agents. The preferred solution for extraction of rHbsAg from washed yeast membranes corresponding to the second solution in step (2), supra, is buffer, containing protease inhibitor(s), and TRITON X-100 at concentrations between about 2% (w/v) and about 0.05% (w/v), most preferably about 0.5% (w/v).

Protein denaturants that are suitable in step (2) for releasing MB rHbsAg, or surface antigen, include the generic class of compounds of formula I. Additional suitable protein denaturants include anions such as $ClO_4^-$ and chaotropic agents.

Step (3), when used, involves the treatment of released rHbsAg to effect passage across a diafiltration membrane. The most preferred solution, corresponding to the third solution of step (3), supra, is 10mM phosphate suffer, pH 7.5, in about 0.1% (w/v) TRITON X-100. Other low salt buffers with low concentrations of detergents or denaturants are readily adaptable at this step, and their exact formulation is well within the scope of the variations and adaptations of the principles of the present invention. Similarly, step (3) may be totally eliminated if the second solution of step (2) has the double effect of releasing MB rHbsAg and promoting its passage across the diafiltration or dialysis membrane. Alternatively, released rHbsAg may simply be physically removed from inside the diafiltration membrane.

The procedure for extracting or releasing MB surface antigen from the washed yeast membrane in steps (1)–(3) may require additional washing, concentration or extraction steps. Selective extraction of MB surface antigen from washed yeast membrane need not require diafiltration. Centrifugation and dialysis are also useful alternative procedures provided that appropriate detergents or denaturants are employed. It is contemplated that steps (1)–(3) may be varied substantially. One or more additional concentration steps may be required, as the case may be.

SOLUBILIZATION

The process of solubilizing the selectively extracted rHbsAg includes 4. treating the filtrate of step (3), or other selectively extracted rHbsAg, with a quantity of denaturing agent in the presence of a reducing agent effective to solubilize the rHbsAg therein; and 5. removing the denaturing agent and the reducing agent, yielding a substantially purified recombinant pre-S1/S2/S hepatitis B antigen, or portion thereof.

Solubilizing is conducted in the presence of one or more denaturing agents and one or more reducing agents, or mixtures thereof. The preferred selection of reagents is urea and dithiothreitol (DTT), in the concentration ranges of between about 1M–8M and 1–10mM, respectively. The most preferred solution for solubilization contains about 4M urea and about 5mM DTT. Buffers or protease inhibitors may be added as desired.

Generally, any denaturant of formula I is suitable and feasible for the purposes of solubilization. This formula includes urea, wherein R is amino, X is O and Y is H. Other denaturants of use in solubilization protocols include, but are not limited to, detergents of the nonoxynol series, octoxynol series, polyoxyethylene alcohol series, polyoxyethylene (20) sorbitan mono-oleate series, deoxycholate, or octylglucopyranoside, and the like. Zwitterionic detergents are also useful and suitable agents.

Reducing agents useful for solubilizing rHbsAg are thiol reagents that will not modify substantially the SH groups of the protein rHbsAg. Cysteine, homocysteine, β-mercaptoethanol, dithiothreitol, dithioerythritol and sodium bisulfite are some of the reagents that fall within the category of such thiol reagents. On the other hand, Ellman's reagent and sodium borohydride are each regarded as too strong for the solubilization reaction, since reaction of rHbsAq with each yields a product of substantially irreversibly modified character not subject to reversible rearrangement and formation of new disulfide linkages among rHbsAg cysteine residues.

ADDITIONAL STEPS

Other conventional or known steps normally used in purification of recombinant proteins may be added to the process of purifying rHbsAg. These steps include, but are not limited to:

(a) selective adsorption or partition on a solid-phase, e.g. silica gel, calcium phosphate charcoal, or celite alumina;

(b) hydrophobic chromatography with, e.g. butyl-agarose, hexyl-agarose, octyl-agarose or phenyl-agarose; and (c) selective extraction with solvents or reagents that release undesired membrane-bound proteins followed by other solvents or reagents that release membrane bound rHbsAg. Extraction with other solvents or reagents for other purposes may be needed in different steps.

(d) Precipitation is another step useful for isolating rHbsAg. It can be performed with salts such as ammonium sulfate, or on a pH gradient by isoelectric precipitation. Other methods include (e) chromatography by any standard method, including paper, thin layer, gel, molecular sieve, molecular exclusion, on-exchange, ligand affinity, immunoaffinity, or by electrophoresis;
(f) solvent fractionation by two phase extractions, e.g. with PEG and dextran [Anderson, E. et al., Ann. N.Y. Acad. Sci. 413, 115 (1983)].
(g) dialysis, ultrafiltration, or diafiltration;
(h) density gradient centrifugation;
(i) electrofocusing;
(j) freeze drying, lyophilization; or
(k) crystallization.

This list is by no means exhaustive. Its order is not an indication of the preferred order of purification. It will be understood that a successful purification of rHbsAg may be conducted with any or all of steps (a)-(k), and that in principle solubilization as described above may be inserted as an additional step at any point.

In the examples the following materials were purchased from commercial sources: Urea and guanidine.HCl, Schwartz/Mann Biotech; TRITON X-100, Fisher Scientific Company; dithiothreitol, Bio Rad.

Throughout this application, glycoprotein was determined by the periodic acid-Schiff base procedure of Neville, D. M. et al., Methods in Enzymology 32, 92 (1974). Protein concentrations were determined by the SDS Lowry assay, e.g. Lowry, 0. H. et al., J. Biol. Chem. 193, 265 (1951); and the Coomassie blue-binding assay, e.g. Bradford, M. M., Anal. Biochem. 72, 248 (1976).

Immunochemical tests were performed on the lots purified according to the following procedures. Binding to polymerized human serum albumin (pHSA) was conducted according to Valenzuela et. al., Biotechnology, 3, 317 (1985). Immunochemical determinants were assayed by a variety of conventional procedures, including AUSRIA ® II-125 (Abbott Labs), and AUSAB ® (Abbott Labs). Biological activity was tested by the mouse potency test.

EXAMPLE 1

Purification of S Antigen, Lot S-31

All purification steps of this example were conducted at 4° C. Frozen cell paste (52 g) of the S antigen synthesizing yeast cells was suspended in 315 ml of PBS containing 1 mM phenylmethylsulfonylfluoride (PMSF), and 1mM EDTA, and the cells were disrupted. Then broken cells were removed from the cell disrupter by flushing with 1.5L of PBS containing 1mM PMSF and 1mM EDTA. The resulting crude extract was centrifuged for 5 minutes at 4,400×g to remove cell debris. A portion of the 4,400×g supernatant (3% of total vol.) was further centrifuged at 100,000 ×g for one hour and the precipitate (yeast membrane fraction) was separated from the soluble fraction. Localization of the recombinant hepatitis S antigen was performed by AUSRIA ® (Abbott).

TABLE I

EFFECT OF CENTRIFUGATION ON LOCALIZATION OF RECOMBINANT HEPATITIS S ANTIGEN IN YEAST

| Preparation | AUSRIA ® mg | Protein mg | Specific Activity µg AUSRIA ® activity/mg protein |
| --- | --- | --- | --- |
| 4,400 × g supernatant | 39.4 | 24.3 | 1.6 |
| yeast membrane fraction | 35.7 | 4.6 | 7.8 |
| soluble fraction | 1.5 | 14.2 | 0.1 |

TABLE I-continued

EFFECT OF CENTRIFUGATION ON LOCALIZATION OF RECOMBINANT HEPATITIS S ANTIGEN IN YEAST

| Preparation | AUSRIA ® mg | Protein mg | Specific Activity µg AUSRIA ® activity/mg protein |
| --- | --- | --- | --- |
| cell debris | 0.95 | 5.8 | 0.2 |

Table I demonstrates that the presence of the S polypeptide was predominately concentrated in the yeast membrane protein. Further manipulations were preformed on the 4,400×g supernatant to avoid the 100,000×g centrifugation step.

(a) Preparation of washed yeast membrane

The 4,400×g supernatant was introduced under positive pressure of 10–15 psi into a diafiltration unit (450 ml capacity) equipped with a hollow fiber membrane (0.2µm, 1ft.²) with a peristaltic pump. Diafiltration with 2.5L of PBS containing 0.2 mM PMSF and 1 mM EDTA, followed by 250 ml of 7M guanidine.HCl, and 200 ml of 3.5 M guanidine.HCl, followed by 2L of 1M guanidine.HCl. then 2L of PBS containing 1mM EDTA, removed membrane bound yeast impurities without removal of the antigen from the membrane. The resulting retentate product was purified antigen bound to membranes (washed yeast membrane).

(b) Extraction of antigen from yeast membrane

Washed yeast membranes, the product of paraqraph (a) of this Example, were incubated for 30 minutes at 4° C. in 1L of 0.5% (w/v) TRITON X-100 in PBS containing 1mM EDTA. The solubilized antigen was separated from the yeast membrane by concentration to 200 ml over a hollow fiber unit (0.2 µm) followed by diafiltration of the yeast membrane with 2.5L of 0.1% (w/v) TRITON X-100 in 10mM phosphate buffer, pH 7.5. The filtrate contained the S antigen and was concentrated over hollow fiber membrane (100,000 NMW, 0.6 ft.²) to 200 ml, then diafiltered with 2L of PBS. The resulting retentate containing the S antigen was incubated in 4M urea containing 5 mM DTT for 15 minutes, and then diafiltered over a hollow fiber membrane (100,000 NMW, 0.6ft²) with 700 ml of 2 mM DTT in 2M Urea followed by 700ml of 2M Urea, then 2L of PBS. The resulting purified antigen (designated S-31) has a high specific activity, as demonstrated by the results of Table II.

TABLE II

PURIFICATION OF MEMBRANE-BOUND RECOMBINANT HEPATITIS S ANTIGEN FROM YEAST BY RELEASE FROM THE MEMBRANE IN PRESENCE OF 0.5% TRITON X-100[1]

| Preparation | AUSRIA ® mg | Protein mg | Specific Activity µg AUSRIA ® activity/mg protein |
| --- | --- | --- | --- |
| crude extract | 12.8 | 7,900 | 1.6 |
| 4,400 × g supernatant | 16.6 | 5,100 | 7.3 |
| washed yeast membrane | 8.4 | 393 | 14 |
| purified antigen (S-31) | 15.1 | 51 | 300 |

[1] Antigen lot number S-31.

A portion of the purified antigen was then treated with 3M KSCN in PBS for 16 hours and diafiltered over hollow fiber membrane (100,000 NMW, 0.6 ft.²) with 500 ml. of 3M KSCN in PBS and 750 ml of 1M KSCN in PBS, then 2L of PBS, yielding lot number S-31/KSCN. Both lots of the purified antigen (S-31 and S-31/KSCN) were examined under electron microscopy and found to contain 20nm particles.

EXAMPLE 2

Mouse Potency

Mouse potency of the purified S antigen (of Example 1) was assessed by procedures as follows. Antigen samples to be tested were sterile filtered, then adsorbed on ALHYDROGEL (Superfos Specialty Chemicals a/s, Vedbaek, Denmark) by adding 1ml to each 20 ml of sample, followed by stirring two hours at room temperature.

Thimerosal was then added to a sample concentration of 1:20,000. The preparation was tested in mice undiluted and diluted in alum placebo to contain 0.025, 0.006 and 0.0016 µg/ml. One milliliter of each preparation, or alum placebo, was injected intraperitoneally into each of 10 mice. The mice were individually bled 28 days later and antibody titers were measured by the AUSAB® radioimmune assay (Abbott). Data were analyzed to determine seroconversion rates to the different doses of subunit HbsAg. A probit analysis was performed, plots of empirical probit versus dose were made, iterative maxium liklihood least squares performed on the data and the $ED_{50}$ values (µg) were obtained.

Results of the mouse potency tests are $ED_{50} = 1.3$ µg for lot S-31 and 1.2 µg for lot S-31/KSCN, showing clear efficacy in vivo.

EXAMPLE 3

Purification of pre-S1/S2/S Antigen

Frozen cell paste (90g) of the pre-S1/S2/S protein synthesizing yeast cells was suspended in 90 ml of PBS containing 1.0mM PMSF, 10mM EDTA and 0.1M Tris HCl, pH 7.5 ("buffer"). The cells were broken in a DYNO-MILL, 5 times for 30 seconds, then the broken cells were removed from the DYNO-MILL by flushing with 1.2L of the buffer. The resulting crude extract was centrifuged for 10 minutes at 4,400×g to remove cell debris. The 4,400×g supernatant was introduced under positive pressure of 10-15 psi into a diafiltration unit (450 ml capacity) equipped with a hollow fiber membrane (0.2 µm, 1 ft²) with a peristaltic pump, and diafiltered with 1.5L of PBS containing 1.0mM PMSF, followed by 300 ml of 7M guanidine.HCl, then 2L of 1M guanidine.HCl, and finally 1.5 L of PBS containing 0.2mM PMSF and 10mM EDTA. The resulting retentate (washed yeast membrane) was incubated for 20 minutes at 4° C. in 1.6L of PBS containing 0.5% TRITON X-100 and protease inhibitors [final concentrations in PBS of 0.2mM PMSF, 10mM EDTA, 0.1% (w/v) pepstatin A, 0.013% (w/v) aprotinin and 10mM benzamidine.HCl]. The solubilized antigen was separated from the yeast membrane by concentration to 200 ml over a hollow fiber unit (0.2µm) followed by diafiltration of the yeast membrane with 1.5L of 10mM sodium phosphate buffer, pH 7.5, containing 0.1% (w/v) TRITON X-100 and the above protease inhibitors. The filtrate contained the antigen, was concentrated over a hollow fiber membrane (100,000 NMW 0.6 ft²) to 200 ml, then diafiltered against 7 volumes of PBS. The retentate, which contained the antigen, was incubated in 5mM DTT in 4M Urea for 15 minutes, then concentrated over a hollow fiber membrane (100,000 NMW, 0.6 ft²) to 200 ml, and as a final step was diafiltered against 5 volumes of 2mM DTT in 2M Urea, then 10 volumes of PBS, yielding purified antigen. The resulting product was examined under electron microscopy and found to be aggregates of usually less than 20 nm diameter.

EXAMPLE 4

The purification steps of Example 1 were repeated, except the pre-S1/S2/S protein synthesizing yeast cells was substituted for S antigen synthesizing yeast cells. The product was a substantially pure recombinant pre-S1/S2/S protein, yielding 20nm particles of surface antigen.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims.

What is claimed is:

1. A method of substantially purifying recombinant pre-S1/S2/S hepatitis B antigen, or portion thereof immunochemically reactive with antibodies specific to natural hepatitis surface antigen, comprising the steps of
    (a) taking an aliquot of yeast membrane associated antigen extract;
    (b) removing the debris of the extract of step (a) by centrifugation;
    (c) subjecting the supernatant to diafiltration in the presence of a solution comprising guanidine-HCl of concentrations varying during the diafiltration from between about 7M and 1M, said solution effective to release undesired yeast membrane-bound proteins, and thereafter removing said undesired yeast membrane-bound proteins to yield washed yeast membrane as a retentate product;
    (d) subjecting the retentate product of step (c) to a second solution comprising a buffered solution containing octoxynol-9.5 at a concentration of between about 0.1% (w/v) and about 1% (w/v), said second solution effective to release the membrane-bound surface antigen;
    (e) subjecting the surface antigen released in step (d) to diafiltration in a third solution to promote passage of said surface antigen across the diafiltration membrane, yielding a filtrate;
    (f) treating the filtrate with a quantity of denaturing agent in the presence of a reducing agent effective to solubilize said filtrate; and
    (g) removing the denaturing agent and the reducing agent, yielding a substantially purified recombinant pre-S1/S2/S hepatitis B antigen, or portion thereof immunochemically reactive with antibodies specific to natural hepatitis surface antigen.

2. The method of claim 1 wherein the diafiltration of step (c) is conducted under positive pressure of about 10-15 psi.

3. The method of claim 1 wherein the diafiltration of step (c) is conducted with a diafiltration apparatus with a hollow fiber membrane having a pore diameter of about 0.2 µm.

4. The method of claim 1 wherein said second solution comprises about 0.5% (w/v) TRITON X-100 in phosphate buffer.

5. The method of claim 1 wherein said second solution comprises about 1.0% (w/v) TRITON X-100 in phosphate buffer.

6. The method of claim 1 wherein said second solution comprises a buffered solution containing TRITON X-100 at a concentration of between about 0.5% (w/v) and about 1.0% (w/v).

7. The method of claim 1 wherein the second solution comprises buffer, and TRITON X-100 in a concentration range of between about 1% (w/v) and about 0.1% (w/v), and protease inhibitors.

8. The method of claim 7 wherein the second solution consists essentially of PBS containing about 0.5% (w/v) TRITON X-100, and about 1mM EDTA.

9. The method of claim 1 wherein the diafiltration of step (e) is conducted with a diafiltration apparatus with a hollow fiber membrane having a pore diameter of 0.2 $\mu$m.

10. The method of claim 1 wherein the third solution of step (e) comprises buffer containing between about 0.05% and 0.5% TRITON X-100.

11. The method of claim 1 wherein the third solution of step (e) comprises phosphate buffer containing about 0.1% TRITON X 100.

12. The method of claim 1 wherein the denaturing agent of step (f) is urea.

13. The method of claim 1 wherein the reducing agent of step (f) is dithiothreitol.

14. The method of claim 1 wherein the denaturing agent in step (f) is urea and the reducing agent in step (f) is dithiothreitol.

15. The method of claim 14 wherein the urea is at a final concentration of about 4M and the dithiothereitol is at a final concentration of about 5mM.

* * * * *